US00PP15119P2

(12) United States Plant Patent
Westhoff

(10) Patent No.: US PP15,119 P2
(45) Date of Patent: Aug. 31, 2004

(54) CALIBRACHOA PLANT NAMED 'WESCADARKBLUE'

(50) Latin Name: ***Calibrachoa* sp.**
Varietal Denomination: Wescadarkblue

(75) Inventor: Heinrich Westhoff, Südlohn (DE)

(73) Assignee: Josef & Heinrich Westhoff Gartenbau-Spezialkulturen, Südlohn-Oeding (DE)

( * ) Notice: Subject to any disclaimer, the term of this patent is extended or adjusted under 35 U.S.C. 154(b) by 0 days.

(21) Appl. No.: 10/602,101

(22) Filed: Jun. 23, 2003

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—C. A. Whealy

(57) ABSTRACT

A distinct cultivar of Calibrachoa plant named 'Wescadarkblue', characterized by its cascading and uniform growth habit; freely branching habit; large flower size; and numerous dark violet-colored flowers.

1 Drawing Sheet

Botanical classification/cultivar designation: Calibrachoa sp. cultivar 'Wescadarkblue'.

BACKGROUND OF THE INVENTION

The present Invention relates to a new and distinct cultivar of Calibrachoa plant, botanically known as Calibrachoa sp., and hereinafter referred to by the cultivar name 'Wescadarkblue'.

The new Calibrachoa is a product of a planned breeding program conducted by the Inventor in Sudlohn-Oeding, Germany. The new Calibrachoa originated from a cross-pollination made by the Inventor of a proprietary selection of Calibrachoa identified as code number 99 FA 228, not patented, as the female, or seed, parent with a proprietary selection of Calibrachoa identified as code number 99 FA 132, not patented, as the male, or pollen, parent. The new Calibrachoa was discovered and selected by the Inventor in 1999 in a controlled environment in Sudlohn-Oeding, Germany as a single plant within the resulting progeny from the cross-pollination.

Asexual reproduction of the new cultivar by terminal cuttings at Sudlohn-Oeding, Germany since 1999, has shown that the unique features of this new Calibrachoa are stable and reproduced true to type in successive generations.

SUMMARY OF THE INVENTION

Plants of the cultivar 'Wescadarkblue' have not been observed under all possible environmental conditions. The phenotype may vary with variations in environment such as temperature, light intensity and daylength without, however, any variance in genotype.

The following traits have been repeatedly observed and are determined to be the unique characteristics of 'Wescadarkblue'. These characteristics in combination distinguish 'Wescadarkblue' as a new and distinct cultivar:

1. Cascading and uniform growth habit.
2. Freely branching habit, dense and bushy.
3. Large flower size.
4. Numerous dark violet-colored flowers.

Plants of the cultivar Wescadarkblue can be compared to plants of the female parent selection. In side-by-side comparisons conducted in Sudlohn-Oeding, Germany, plants of the new Calibrachoa differed from plants of the female parent selection in the following characteristics:

1. Plants of the new Calibrachoa had smaller and narrower leaves than plants of the female parent selection.
2. Plants of the new Calibrachoa had larger flowers than plants of the female parent selection.
3. Plants of the new Calibrachoa and the female parent selection differed in flower color as plants of the female parent selection had red purple-colored flowers.

Plants of the cultivar Wescadarkblue can be compared to plants of the male parent selection. In side-by-side comparisons conducted in Sudlohn-Oeding, Germany, plants of the new Calibrachoa differed from plants of the male parent selection in the following characteristics:

1. Plants of the new Calibrachoa had a more uniform plant form than plants of the male parent selection.
2. Plants of the new Calibrachoa had shorter internodes than plants of the male parent selection.
3. Plants of the new Calibrachoa had larger flowers than plants of the male parent selection.

Plants of the new Calibrachoa can also be compared to plants of the Calibrachoa cultivar Wesviolet, disclosed in U.S. Plant Pat. No. 12,584. In side-by-side comparisons conducted in Sudlohn-Oeding, Germany, plants of the new Calibrachoa differed from plants of the cultivar Wesviolet in the following characteristics:

1. Leaves of plants of the new Calibrachoa were broader and lighter green in color than leaves of plants of the cultivar Wesviolet.
2. Plants of the new Calibrachoa had larger flowers with larger sepals than plants of the cultivar Wesviolet.
3. Flowers of plants of the new Calibrachoa were darker violet in color than flowers of plants of the cultivar Wesviolet.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Calibrachoa.

The photograph at the top of the sheet is a close-up view of typical flowers of 'Wescadarkblue'.

The photograph at the bottom of the sheet comprises a side perspective view of a typical flowering plant of 'Wescadarkblue'.

DETAILED BOTANICAL DESCRIPTION

Plants used in the aformentioned photographs and for the following description were grown under conditions which closely approximate commercial production conditions during the spring and summer in a glass-covered greenhouse in Sudlohn-Oeding, Germany. Plants were about 20 weeks from planting rooted cuttings in 12-cm containers. During the production of the plants, the day temperatures ranged from 20 to 25° C., night temperatures ranged from 16 to 18° C., and light levels ranged from 3,000 to 50,000 lux.

In the following description, color references are made to The Royal Horticultural Society Colour Chart, 2001 Edition, except where general terms of ordinary dictionary significance are used.

Botanical classification: Calibrachoa sp. cultivar 'Wescadarkblue'.

Parentage:

*Female parent.*—Proprietary selection of Calibrachoa sp. identified as 99 FA 228, not patented.

*Male parent.*—Proprietary selection of Calibrachoa sp. identified as 99 FA 132, not patented.

Propagation:

*Type cutting.*—Terminal vegetative cuttings.

*Time to initiate roots.*—About 18 to 20 days at 20° C.

*Time to develop roots.*—About 20 to 28 days at 20° C.

*Root description.*—Numerous, fine, fibrous, and well-branched.

Plant description:

*Form.*—Annual flowering plant; cascading; uniform, rounded appearance, plants eventually become spherical in overall shape. Freely branching with lateral branches forming at every node. Vigorous growth habit.

*Usage.*—Appropriate for hanging baskets, window boxes and patio containers.

*Plant height* (*from soil level to top of plant plane*).—About 7 to 17 cm.

*Plant length* (*from soil level to lateral branches apices*) .—About 80 to 104 cm.

*Plant diameter* (*area of spread*).—About 65 cm.

*Stem description.*—Main branches, length: About 66 cm. Main branches, diameter: About 2.4 mm. Lateral branches, length: About 41 cm. Lateral branches, diameter: About 1.1 mm. Internode length: About 2 cm. Texture: Pubescence. Strength: Strong, wiry. Color: 146B to 146C.

*Foliage description.*—Leaves simple, generally symmetrical and long persisting; sessile. Arrangement: Alternate. Length: About 2.8 cm. Width: About 7 mm. Shape: Lanceolate. Apex: Obtuse to rounded. Base: Attenuate. Margin: Entire. Aspect: Mostly flat. Texture, upper and lower surfaces: Slightly pubescence. Venation: Pinnate; only midvein visible. Color: Developing foliage, upper surface: 146A. Developing foliage, lower surface: 146B. Fully expanded foliage, upper surface: 137B; midvein, 137C. Fully expanded foliage, lower surface: 137C; midvein, 137D.

Flower description:

*Flower type and habit.*—Large-sized flowers; flowers face upright or outward; single, axillary. Flowers not persistent. Freely flowering with flowers forming at every axil.

*Natural flowering season.*—Spring until frost in the autumn; flowering continuous.

*Flower longevity on the plant.*—About one week.

*Flower size.*—Diameter: About 3.2 cm. Depth (height): About 2 cm. Tube length: About 1.8 cm. Throat diameter, distal end: About 8 mm. Tube diameter, proximal end: About 3 mm.

*Flower buds.*—Length: About 2.3 cm. Diameter: About 5 mm. Shape: Oblong. Color: 154C; venation, N79A; towards the apex, 83B.

*Corolla.*—Arrangement/appearance: Single whorl of five petals, fused into flared trumpet. Petal length from throat: About 1.3 cm. Petal width: About 1.4 cm. Petal shape: Nearly rounded with rounded apex. Petal margin: Entire. Petal texture: Smooth, satiny. Color: Petal, upper surface, when opening: 83A to 83B. Petal, lower surface, when opening: 83B to 83C. Petal, upper surface, opened flower: 83B; venation, 79A; color becoming closer to 83B to 83C with development. Petal, lower surface, opened flower: 83C; venation, 79A to 79B. Flower throat (in side): 13B to 13C; venation, 79A. Flower tube (outside): 154C; venation, 79A.

*Sepals.*—Arrangement/appearance: Single whorl of five sepals, star-shaped. Length: About 1.3 cm. Width: About 3 mm. Shape: Lanceolate. Apex: Acute. Margin: Entire. Texture, upper and lower surfaces: Pubescent. Color, upper and lower surfaces: 137B to 137C.

*Peduncles.*—Length: About 2.2 cm. Width: About 0.8 mm. Strength: Flexible, wiry. Color: 144A.

*Reproductive organs.*—Stamens: Quantity per flower: Five. Anther shape: Four-parted, oval. Anther length: About 1.1 mm. Anther diameter: About 1.1 mm. Anther color: 13B. Pollen amount: Moderate. Pollen color: 13B to 13C. Pistils: Quantity per flower: One. Pistil length: About 1 cm. Stigma shape: Oval. Stigma color: 144A. Style length: About 0.8 mm. Style color: 144D. Ovary color: 144B to 144C.

*Seed/fruit.*—Seed and fruit production has not been observed.

Disease/pest resistance: Plants of the new Calibrachoa have not been noted to be resistant to pathogens and pests common to Calibrachoa.

Temperature tolerance: Plants of the new Calibrachoa have been observed to be tolerant to temperatures ranging from 2 to 30° C.

It is claimed:

1. A new and distinct cultivar of Calibrachoa plant named 'Wescadarkblue', as illustrated and described.

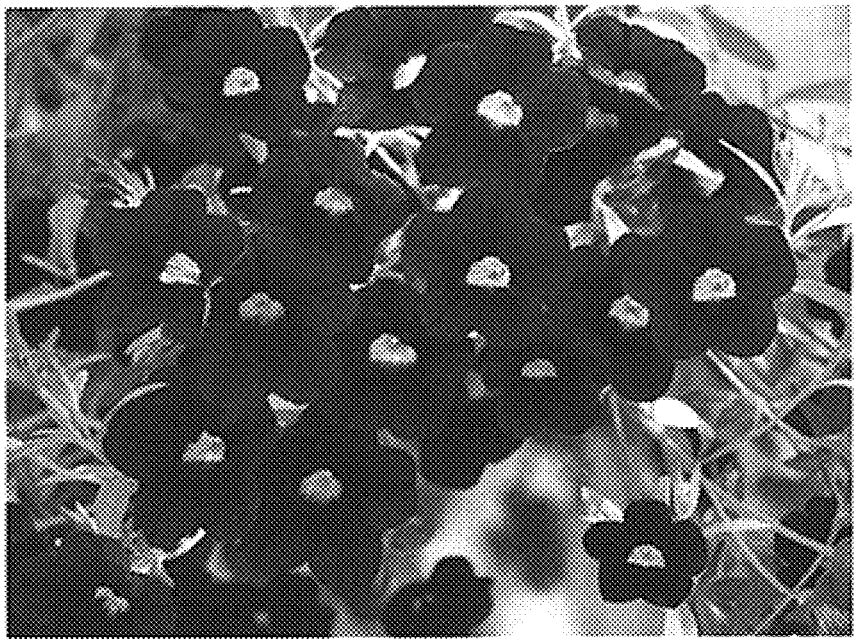
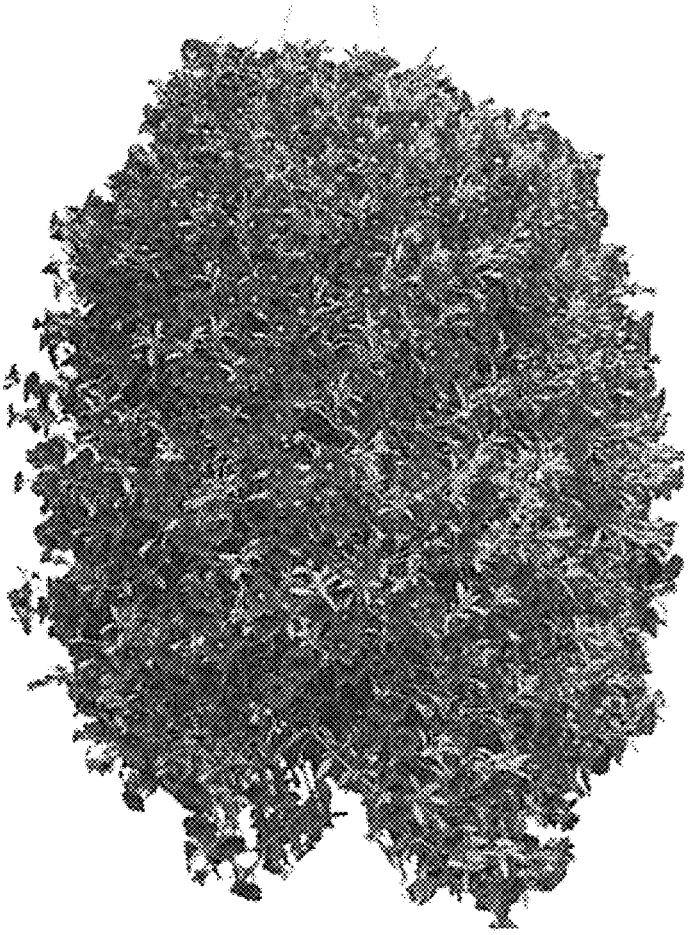

* * * * *